Figure 1:
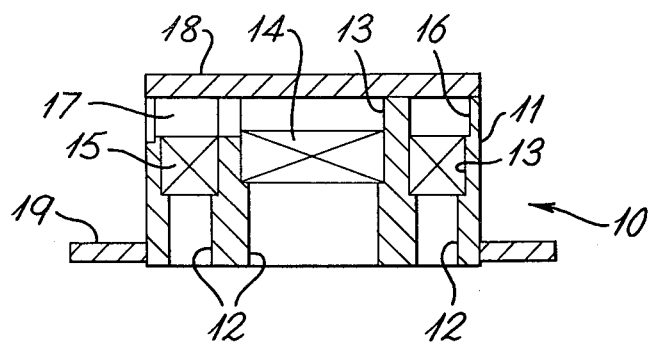

United States Patent [19]

Mott

[11] 4,414,980
[45] Nov. 15, 1983

[54] BLOOD FLOW MONITOR APPARATUS

[75] Inventor: Godfrey T. Mott, Ruislip, England

[73] Assignee: National Research Development Corporation, London, England

[21] Appl. No.: 267,606

[22] Filed: May 27, 1981

[30] Foreign Application Priority Data

May 29, 1980 [GB] United Kingdom ............... 8017845

[51] Int. Cl.³ .............................................. A61B 5/02
[52] U.S. Cl. .................................................. 128/664
[58] Field of Search ............................... 128/633–634, 128/664, 666, 687–690

[56] References Cited

U.S. PATENT DOCUMENTS

| 3,825,342 | 7/1974 | Lubbers et al. | 128/634 |
| 4,086,915 | 5/1978 | Kofsky et al. | 128/633 |
| 4,163,447 | 8/1979 | Orr | 128/690 |
| 4,224,948 | 9/1980 | Cramer et al. | 128/690 |
| 4,295,470 | 10/1981 | Shaw et al. | 128/634 |

OTHER PUBLICATIONS

Dimmick, R. F. et al., "Optical Plethysmograph" IBM Tech. Disclosure Bulletin, vol. #3, Aug. 1976, pp. 772–773.

Primary Examiner—Kyle L. Howell
Assistant Examiner—Francis J. Jaworski
Attorney, Agent, or Firm—Cushman, Darby & Cushman

[57] ABSTRACT

Blood flow monitor apparatus includes a transducer having a skin-engaging face from which first and second light guides respectively lead to a photodetector and light source, the second light guide forming an array surrounding the first at said face. There can be a plurality of second light guides leading to respective individual sources or, by bundling guides of fibre optic form, to a single source. In the latter case the source can be remotely connected by a fibre optic cable to a separate skin probe. Infra-red operation is preferred. The apparatus will also normally involve a visual display of, and an alarm responsive to attainment of a preset level for, at least one characteristic of the detector output. The first time differential is a characteristic of particular interest, and a presently preferred characteristic is the ratio between the maximum and minimum values of this differential.

8 Claims, 8 Drawing Figures

BLOOD FLOW MONITOR APPARATUS

The present invention has been initially conceived and developed for use in association with plastic surgery, and more particularly so-called free flap transfers in which a section of healthy tissue is wholly removed from one part of the body and re-implanted in another part needing tissue cover. The operation for such a transfer takes many hours and involves communication by microsurgery of the blood vessels in the transferred tissue section with others in its new site. This operation takes many hours but, if successful, replaces other procedures involving several long operations over a period of many months and lengthy immobilisation of the patient.

The success of the free flap transfer procedure depends on an adequate blood supply being maintained in the transferred tissue section, especially during the first few hours post-operatively. In the past, surgeons have relied upon a clinical impression of temperature and colour in the section to assess the state of blood perfusion, with ultimately the only certain way to establish the existence of perfusion being to cut the skin of the section. Inevitably such techniques can be accompanied by a delay of several hours before a vascular problem becomes evident and surgical correction is undertaken. Such a delay can prejudice complete recovery because the lack of adequate blood supply can cause irreversible damage.

The present invention seeks to improve the above situation and has proved satisfactory in clinical trial.

The invention centers on a transducer having a face for application to the skin, a photoelectric detector, first light guide means extending between said detector and said face, a light source, and second light guide means extending between said source and said face to terminate at said face in an array surrounding said first light guide means.

In use of this transducer, the relevant face is applied to the skin, the light source is energised to radiate by way of the second light guide means into the skin and underlying tissue, and the detector responds to the light reflected back into the first light guide means after scattering in the tissue. The amount of light detected in this way depends upon the reflection characteristics of the tissue and this changes as the blood content varies with pulsatile flow.

Preferably the light source is of infra-red form and the detector is correspondingly infra-red responsive. This minimises the effect of any extraneous light and also maximises the sensitivity because infra-red light has a greater depth of penetration in tissue than visible light.

Initial development of the invention has shown that light radiation in a generally annular array aound a central detection area to flood the underlying tissue in a relatively uniform manner is appropriate to the provision of an output from the detector which consistently and reliably represents the tissue blood content. A suitable form of the proposed transducer for general purposes comprises a housing carrying the detector and a plurality of separate light sources, the detector and sources being located in a recessed manner respectively within a central bore and an annular array of further bores therearound to serve as light guides. Further development of the invention has also led to an alternative form of transducer in which light guide means of fibre optic form are employed to convey light from a single light source to the required array and to the detector. This alternative form facilitates reduction of the skin-application face of the transducer, with remote location of the light source and detector, and is suited to special-purpose usage.

Use of the invetion will normally involve a blood flow monitor apparatus comprising the proposed transducer in association with means providing a visual display of the transducer response and such means can show one or more characteristics of the response. One display, suitably of digital form, can indicate the level of light detected, P, of which the mean, Po, is thought to provide information relating to the overall level of blood perfusion. Another display, suitably of graphical form, can show the changes $\Delta P$ in the level of light detected. This second characteristic varies with pulsatile flow and can accordingly indicate perfusion activity, but it also varies with changes in cardiac output related to respiration and so may be unstable for clinical monitor purposes. A further display, also suitably of graphical form, can show the rate of change of $\Delta P$ with time, $dP/dt$, and is not only very stable but demonstrates considerable advantages in terms of waveform analysis.

Initial development of the invention has involved the display of a plurality of characteristics such as just mentioned in order to assess their value in providing a clinically viable indication of the adequacy of the post-operative blood flow in transferred tissue. This development has led to the finding that a single characteristic can give such an indication in a relatively definitive manner, this characteristic being the ratio between the maximum and minimum values of $dP/dt$. On the basis of clinical experience to date: this ratio indicates a need for surgical correction if it falls, when taken as maximum-to-minimum, to a value of about 1.2; the initial post-operative ratio value is normally about 1.8 followed by a rise with time in a satisfactory situation; and the corresponding ratio value for normal healthy tissue is up to about 3.0 dependent, among other things, upon the measurement site on the body.

It is accordingly preferred to employ this ratio as the principal output from the apparatus for the purpose of generating an alarm, but the usefulness of other characteristics is not discounted.

The invention will, in any case, often be used in circumstances when an ECG monitor is also employed and the latter can be of assistance in the analysis of characteristics displayed as waveforms.

Figure 2:
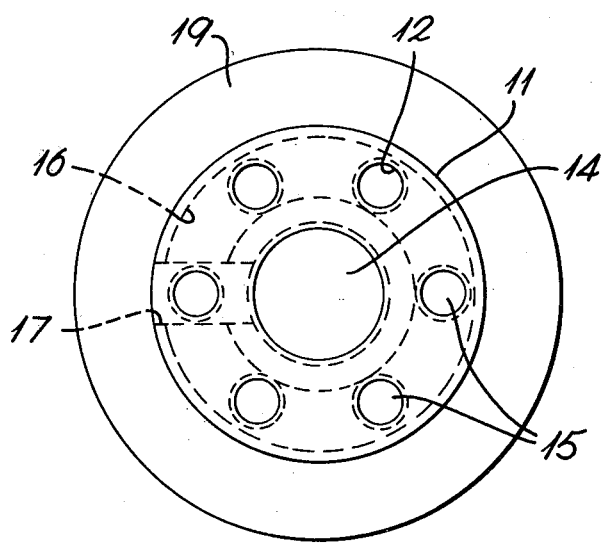
Figure 3:
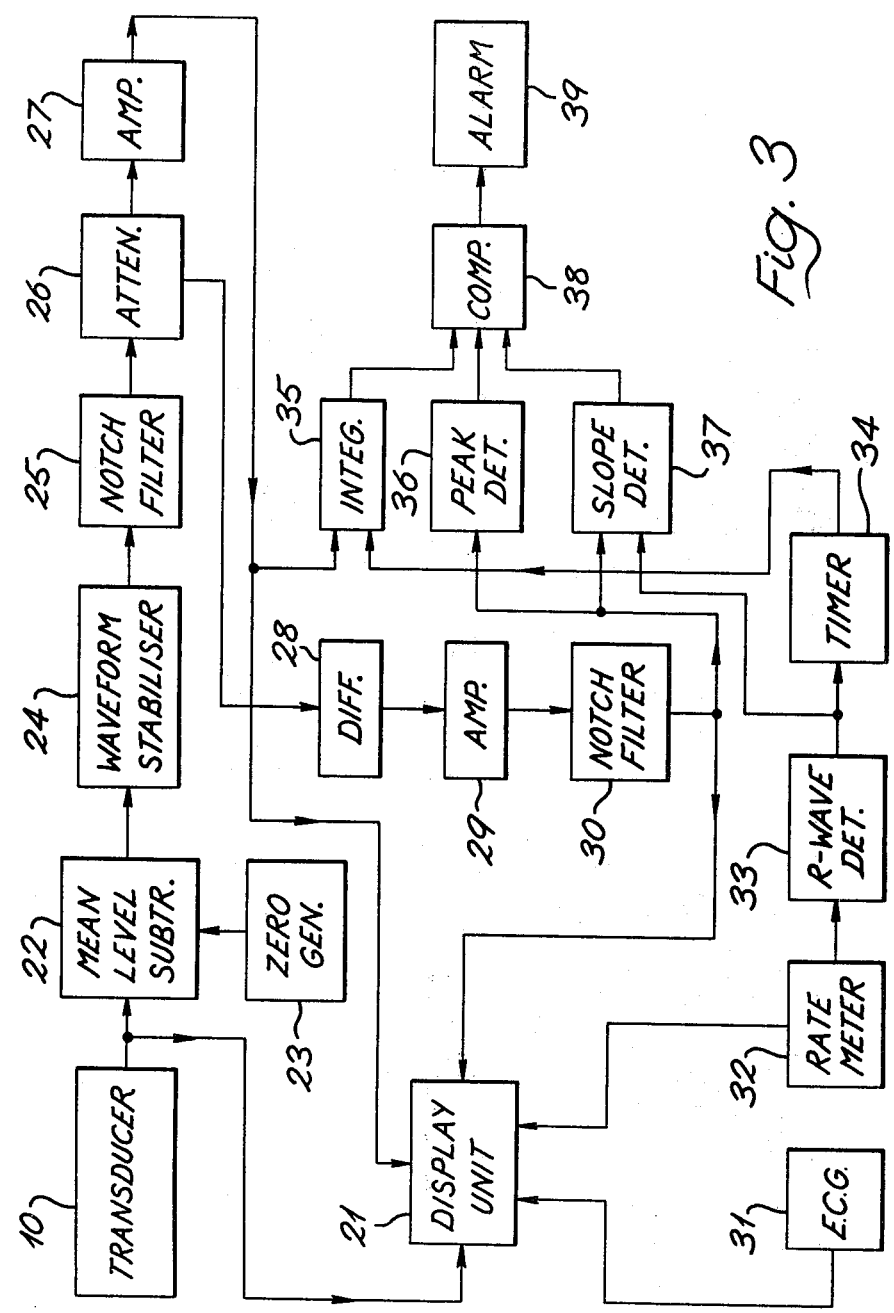
Figure 4:
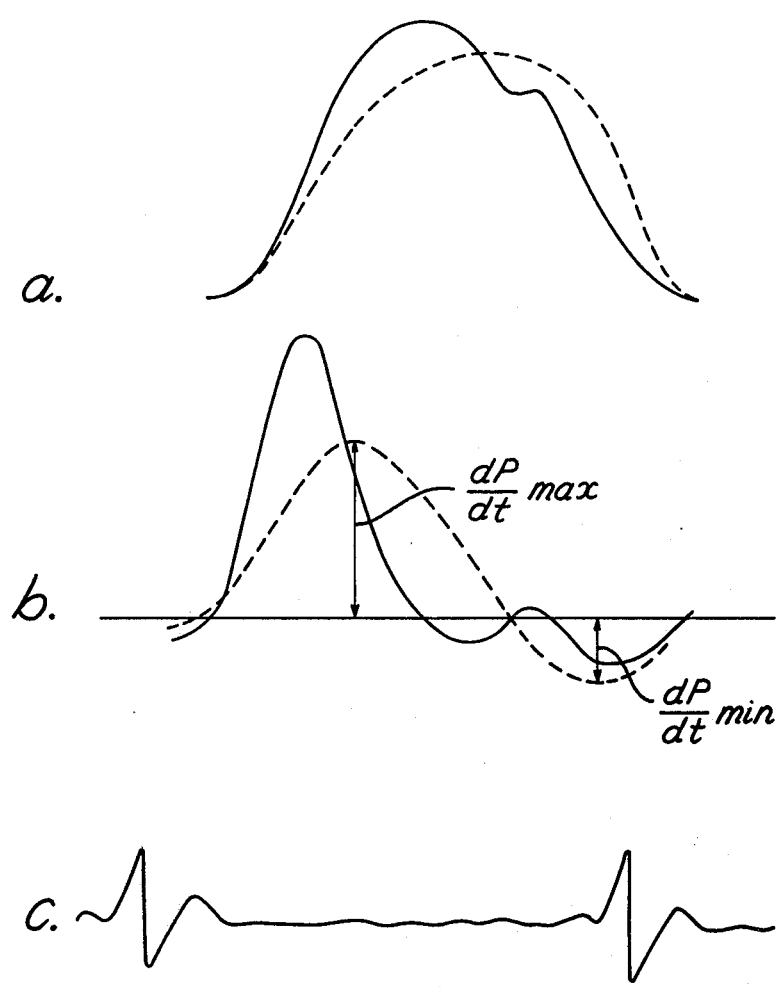
Figure 5:
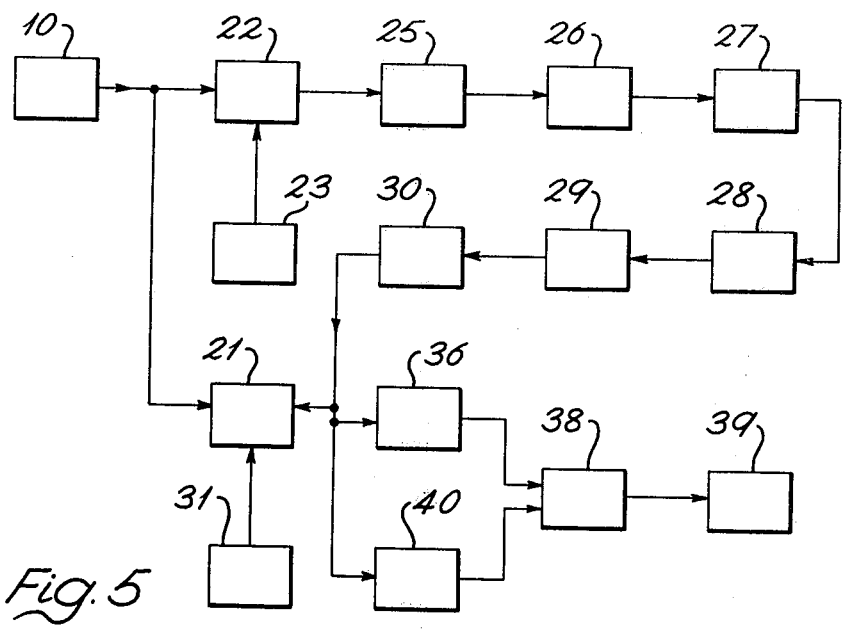
Figure 6:
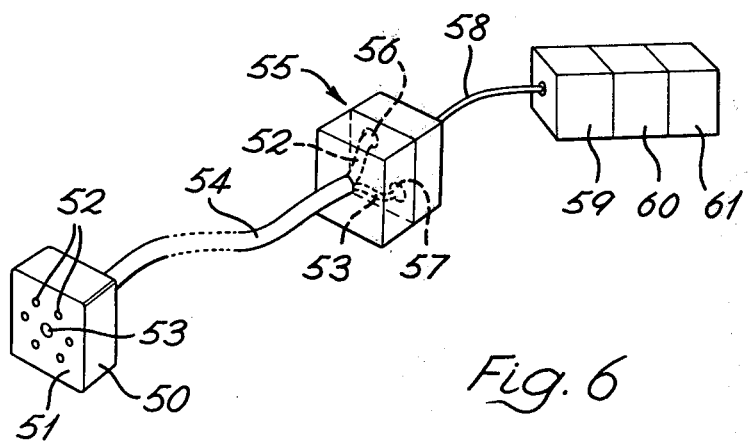

In order to further clarify the invention the same will now be described, by way of example with reference to the accompanying drawings, in which:

FIGS. 1 and 2 respectively illustrate in sectional and end views a transducer resulting from initial development of the invention;

FIG. 3 schematically illustrates an overall apparatus developed with the transducer of FIGS. 1 and 2;

FIG. 4 graphically illustrates the form of outputs produced by the apparatus of FIG. 3;

FIG. 5 schematically illustrates the overall apparatus of a further development of the invention; and FIG. 6 diagramatically illustrates an alternative form of transducer resulting from further development of the invention.

The transducer of FIG. 1 is denoted generally by reference numeral 10 and comprises a body 11 of circular cylindrical form which is longitudinally bored at 12 and counterbored at 13 to receive an infra-red photodiode 14 in an axial location and six infra-red light-emitting diodes 15 in respectively separate locations uniformly spaced around the photodiode 14. The photodiode and diodes are seated in the counterbores to be recessed in the body, and so are effectively collimated in operation to avoid direct action of the latter on the former during use. The outer ends of the diode counterbores are communicated by an annular groove 16, and a radial groove 17 communicates the annular groove with the photodiode counterbore and the transducer exterior. These grooves allow suitable leads to be connected, the grooved end of the body then being closed by a plate 18 and the transducer hermetically sealed.

The transducer body is provided with a radial collar 19 adjacent to, but slightly set back from, its end further from the plate 18.

The use of the transducer will be evident from the introductory discussion above and involves location against the skin of a transferred tissue section whereby the diodes flood the subcutaneous tissue in the field of view of the photodiode which responds to scattered reflections. The collar assists in excluding extraneous light and also facilitates attachment of the transducer to the skin by use of double-sided adhesive tape on the forward face of the collar. This mode of attachment is further advantageous by virtue of the forward face of the transducer being slightly proud of the collar and produces a generally reproduceable, but not high, contact pressure which increases sensitivity without restricting blood flow.

In the present embodiment the diodes are of a type (Radio spares 308067) having a peak spectral output at 940 nm. The associated photodiode is of a type having an integral amplifier (both from Radiospares Optoswitch 307913), a peak spectral response at 900 nm, a linear response (60 V/$\mu$W/cm$^2$) and a fast response time (30 $\mu$s).

Considering now the overall apparatus of FIG. 3, the output of the transducer 10 is applied directly to a digital voltmeter in a display unit 21 to indicate the level of light detected, P. The transducer output is additionally applied to a mean level subtractor 22 having a zero generator 23. The subtractor 22 has a long time constant compared to the incoming pulsatile signal and is operable to subtract substantially all of the unvarying components and to amplify the dynamic components. These amplified components are applied to a waveform stabiliser 24 to reduce the effects of gross changes arising from patient movement, extraneous light, etc., and then through a notch filter 25 to remove mains interference, particularly from ambient lighting sources, and after attenuation at 26 and amplification at 27, a pen recorder and/or oscilloscope in the display unit 21 to show $\Delta$P.

The output from the attenuator 26 is also applied to a differentiator 28, and then by way of an amplifier 29, and a notch filter 30 to remove interference at double mains frequency emitted by some fluorescent lights, to the display 27 to show dP/dt.

An associated ECG monitor 31 also has its output applied to the display 27, and by way of a ratemeter 32 which can also be used to indicate pulse rate in the display unit 21, R-wave detector 33 and timer 34 to a monitor alarm system. This system compares the actual values of specific characteristics derived from the transducer output with preset values selected for an individual patent, and an alarm is activated when a persistent difference is detected. One such characteristic is the integral of $\Delta$P and is derived from an integrator 35 to which the outputs from timer 34 and amplifier 26 are applied, the timer controlling integration to extend over cardiac cycle periods. Another such characteristic is the peak height of dP/dt which is provided by a peak detector 36 responsive to the output of filter 30. Other such characteristics can be the rise and fall times of the dP/dt output from the filter 30 and involve a slope detector 37. The associated comparator is denoted generally at 38 and the alarm, which can be of aural and/or visual form, at 39. The alarm also preferably responds to an absence of pulse output from the transducer.

FIG. 4 shows in solid line form for a healthy transfer typical output waveforms resulting from the apparatus of FIG. 3 in respect of (a) $\Delta$P, (b) dP/dt, and (c) ECG as presented simultaneously on a pen recorder. The $\Delta$P waveform exhibits a sharp rise at the outset of systole as the blood pulse arrives at the capillary bed in the transferred section. The rate of rise relates directly to the rate of inflow of blood, and the amplitude therefore depends on the blood volume. However, the rate of rise is also affected by resistance to outflow. In cases of venous congestion, which is a common condition in the early post-operative period, the peak is reduced in height, delayed in time, and the rate of rise is lower, as indicated in broken line. These changes may be subtle, even when physiological changes are gross, and dP/dt is seen to be advantageous in this context. This second waveform is dominated by the peak which corresponds to the upstroke in $\Delta$P. In venous congestion the changes as shown in broken outline are much more evident. As the rate of blood inflow is reduced by an increased back pressure, the height of the peak, which corresponds to the maximum rate of rise in $\Delta$P, is reduced and delayed, and the downstroke is prolonged.

When any problem arises with arterial input, the amplitudes of both $\Delta$P and dP/dt are significantly reduced.

As indicated in the introductory passages above, continued development of the invention has shown that a simplified apparatus is clinically viable with reliance placed on the monitoring of a single characteristic to indicate whether the post-operative blood flow in transferred tissue is satisfactory.

FIG. 5 schematically illustrates such an apparatus as derived from that of FIG. 3, with corresponding component parts being identified similarly. The principal changes, apart from omissions, are that there are now two pek detectors 36 and 40 respectively providing outputs representing the maximum and minimum levels of dP/dt, and the comparator provides an output representing the ratio between these values. The alarm 39 is arranged for activation when the ratio falls to 1.2 and, as before, in the absence of a pulse output. The constituents of the ratio are indicated in FIG. 3(b) relative to the broken line curve, from which it can be seen that the ratio falls significantly with venous congestion compared to the corresponding ratio without such congestion.

Further simplification can involve omission of the amplifier 27, and also display of characteristics other than the ratio of immediate interest and dP/dt, except so far as an associated ECG monitor may still be employed. Also, the alarm may be of multi-step operational form to give additional indication of fall of the ratio value towards 1.2 as a warning to personnel to monitor the situation closely.

Mention has also been made of an alternative form of transducer of which one example is illustrated in FIG.

6. In this example the transducer comprises a block 50 in which are mounted a plurality of separate fibre optic guides terminating at a flat face 51 of the block in an annular array of guides 52 surrounding a central guide 53. The geometry of the guides in face 51 corresponds to that of the bores 12 in FIG. 1 but is much reduced in scale, suitably from a 1½ inch diameter array in FIG. 1 to about one quarter scale.

The guides 52 and 53 are collectively led in the form of a flexible cable 54 to one part of a two-part block 55 of which the parts are releasably clamped together. In the block 55 the guides 52 are conformed into a bundle of which the free ends face a single light source 56 in the opposed part of the block, and the guide 53 is similarly faced towards a detector 57. Respective energisation and output leads for the light source and detector pass as a cable 58 to a further block incorporating a preamplifier 59, mains frequency filter 60 and terminals 61 for connecting the alternative transducer assembly in place of the transducer 10 of FIGS. 1 or 5.

The separable block 55 is beneficial in allowing disconnection for sterilisation that part of the transducer which contacts the patient, it being noted that the separable part in question contains no electrical components. The provision of additional amplification and filtering takes account of the fact that the transducer output of interest will be weaker. Regarding practical application of the alternative transducer, it is typically suited to deployment at small sites such as in the case of digital transfer of toe-to-finger form.

While the present invention has been described with more particular reference to specific embodiments thereof and applications therefor, it is not intended to be limited thereby. The transducer and related apparatus are clearly capable of variation, the former in terms of detailed form and construction, and the latter in terms of signal analysis and in the number and choice of parameters, for example. Regarding application of the invention: this is more generally relevant to any situation where a knowledge of perfusion in an area of skin allows evaluation of the patency of underlying blood vessels, for example, on invarious replants and during vascular surgery.

What is claimed is:

1. A blood flow monitor apparatus comprising a transducer having a face for application to the skin, a photoelectric detector, first light guide means extending between said detector and said face, a light source, second light guide means extending between said source and said face to terminate in an array surrounding said first light guide means, means for providing a first signal representing the rate of change with time of the output from said detector, and means for providing a second signal representing the ratio between the maximum and minimum values of said first signal.

2. Apparatus according to claim 1 wherein said transducer comprises a body housing in recessed manner said detector and a plurality of separate light sources, said body having a plurality of individual bores therein leading at one set of corresponding ends to said face and at their other set of corresponding ends respectively to said detector and separate sources, said bores serving as said first and second light guide means.

3. Apparatus according to claim 2 wherein said body has a collar extending radially therefrom adjacent to said face, but set back therefrom by a small distance compared to the width of said collar.

4. Apparatus according to claim 1 comprising a single light source, and wherein said light guide means are each of fibre optic form with said second light guide means being conformed, remotely from said face, to a bundle having its composite end facing said source.

5. Apparatus according to claim 4 comprising a two-part separably clamped block of which one part houses said first light guide means and said bundle respectively in facing disposition with said detector and said source which are housed in the other part of said block.

6. Apparatus according to claim 1 wherein said light source is of infra-red form and said detector is correspondingly infra-red sensitive.

7. Apparatus according to claim 1 comprising an alarm operable in response to said second signal when representing a preset value for said ratio.

8. Apparatus according to claim 1 wherein said preset value is about 1.2 for said ratio when expressed as maximum-to-minimum.

* * * * *